(12) United States Patent
Albinsson et al.

(10) Patent No.: US 9,650,887 B2
(45) Date of Patent: May 16, 2017

(54) SUBSEA LEAK-DETECTING SYSTEM

(71) Applicant: Aker Subsea AS, Lysaker (NO)

(72) Inventors: Bengt-Åke Albinsson, Bengtsfors (SE);
Lars Timberlid Lundheim, Oslo (NO);
Roy Stensgaard, Stavern (NO)

(73) Assignee: Aker Subsea AS, Lysaker (NO)

( * ) Notice: Subject to any disclaimer, the term of this patent is extended or adjusted under 35 U.S.C. 154(b) by 15 days.

(21) Appl. No.: 14/409,835

(22) PCT Filed: Jul. 16, 2013

(86) PCT No.: PCT/NO2013/000034
§ 371 (c)(1),
(2) Date: Dec. 19, 2014

(87) PCT Pub. No.: WO2014/014356
PCT Pub. Date: Jan. 23, 2014

(65) Prior Publication Data
US 2015/0285060 A1    Oct. 8, 2015

(30) Foreign Application Priority Data

Jul. 17, 2012   (NO) .................................. 20120822

(51) Int. Cl.
| E21B 47/00 | (2012.01) |
| E21B 47/10 | (2012.01) |
| E21B 43/01 | (2006.01) |
| F17D 5/02 | (2006.01) |
| G01M 3/00 | (2006.01) |

(Continued)

(52) U.S. Cl.
CPC .......... *E21B 47/1025* (2013.01); *E21B 43/01* (2013.01); *E21B 43/0122* (2013.01); *E21B 47/00* (2013.01); *E21B 47/01* (2013.01); *E21B 47/10* (2013.01); *E21B 47/102* (2013.01); *F17D 5/02* (2013.01); *G01M 3/00* (2013.01); *G01M 3/007* (2013.01); *G01M 3/16* (2013.01); *G01N 33/1826* (2013.01)

(58) Field of Classification Search
CPC .. E21B 43/0122; E21B 47/0001; E21B 47/01; E21B 47/1025
USPC ........................................... 166/337
See application file for complete search history.

(56) References Cited

U.S. PATENT DOCUMENTS 3,063,500 A    11/1962  Logan
3,877,520 A *   4/1975  Putnam ................... 166/366
(Continued)

FOREIGN PATENT DOCUMENTS

CN    101344003 A    1/2009
CN    201569553 U    9/2010
(Continued)

OTHER PUBLICATIONS

Pino, Gabriel, "International Search Report" for PCT/NO2013/000034, as mailed Nov. 21, 2013, 4 pages.

*Primary Examiner* — Matthew R Buck
*Assistant Examiner* — Aaron Lembo
(74) *Attorney, Agent, or Firm* — Winstead PC

(57) ABSTRACT

A subsea leak detection system for an off-shore operation facility includes a leak detector operatively connected to a controller located on a subsea assembly. The system is provided with a floating member on which the leak detector is suitably attached. The floating member is adapted to be installed and stably positioned, above the assembly.

7 Claims, 5 Drawing Sheets

(51) Int. Cl.
*G01M 3/16* (2006.01)
*E21B 47/01* (2012.01)
*G01N 33/18* (2006.01)

(56) References Cited

U.S. PATENT DOCUMENTS

| | | | |
|---|---|---|---|
| 3,932,853 | A | 1/1976 | Cannon |
| 4,282,487 | A | 8/1981 | Warren et al. |
| 7,918,126 | B2 | 4/2011 | McStay et al. |
| 8,017,928 | B2 * | 9/2011 | McStay ............... G01N 21/645 250/458.1 |
| 9,217,315 | B2 * | 12/2015 | Mogedal ............... E21B 33/037 |
| 2009/0078028 | A1 | 3/2009 | McStay et al. |
| 2010/0051286 | A1 | 3/2010 | McStay et al. |
| 2010/0274491 | A1 | 10/2010 | Andersen et al. |

FOREIGN PATENT DOCUMENTS

| | | |
|---|---|---|
| WO | WO-2007086754 A1 | 8/2007 |
| WO | WO-2009013503 A1 | 1/2009 |
| WO | WO-2010103002 A2 | 9/2010 |

\* cited by examiner

SUBSEA LEAK-DETECTING SYSTEM

FIELD OF THE INVENTION

The present invention in general, relates to a subsea leak detection system and to a method for installation thereof.

More specifically, the present invention relates to a subsea leak detection system which is adapted to be precisely, securely and conveniently positioned at an appropriate sub sea location. This facilitates precise detection of hydrocarbon and other leakage from a subsea assembly, such as a X-mas tree. Hence, is achieved triggering of a message to the well supervising team for initiating corrective steps.

More particularly, the present invention relates to a subsea leak detection system and to a method of positioning such leak detection system appropriately in a subsea location.

TECHNICAL BACKGROUND OF THE INVENTION

It is known in the art that various subsea assemblies are applied in the exploration and production of hydrocarbons such as oil and gas. These include complex installations with various equipment and assemblies. Such assemblies may be X-mas trees, BOPs, production manifolds and so on, as known to persons skilled in the art.

Small and large scale leakages of hydrocarbons and other undesirable materials such as injecting fluids and chemicals are known to occur from such subsea assemblies, particularly during production, resulting in discharge of hydrocarbons or other chemicals to the surrounding water.

Environmental impact analysis of hydrocarbon leakage is today a matter of concern all over the world. Hence, hydrocarbon exploration and production agencies are now attaching immense importance on regulating and substantially preventing hydrocarbon and other leakage from subsea units, not only from economic points of view, but in particular due to environmental concerns.

In the above context, it is hereby clarified that hereinbefore and hereinafter, the present invention as well its technical background, prior art already known, are explained with reference to hydrocarbons, X-mas trees, production units/equipments. It should be understood that these are all limitations for the sake of explanation. The present invention pertains to all types of leakage detection under water such as hydrocarbons, hydraulic fluids and chemicals and so on. Further, the present invention is applicable in respect of all types of units, installations, equipment and subsea assemblies such as X-mas tree, production manifolds and so on, as known to persons skilled in the art, involved in hydrocarbon recovery by offshore operations. Reference to subsea hydrocarbon production units and operations, is purely exemplary and non-limiting.

Application of acoustic methods for subsea leak detection has found applicability for quite a long time, but has suffered from the disadvantage of sensitivity to shadowing of signals by subsea structures and units. However, it is known that such disadvantages are effectively overcome by deploying a plurality of leak detectors around potential leakage zones.

Biosensors, depending on study of the behaviour of the aquatic animals to pollution are known to be effective at shallower levels. However, such sensors are now mainly under experimentation.

Capacitive sensors measure the change in dielectric constant of the medium surrounding the sensor and are found to be fairly and reasonably reliable in precise detection of hydrocarbon and other leakages from subsea production units.

Prevention of hydrocarbon leakage of any scale during subsea production has become increasingly more important. The earlier a small leak can be detected the easier it will be to prevent any major leakage. A significant problem encountered in this respect is toe position the leak detector so that it will correctly detect a leakage.

Proper positioning of the leak detection system is required not only for precise detection of leakage, but also for ensuring that detection of natural seepage from the sea bed does not trigger the leak detector. Natural seepage may trigger wrong signals to the leakage management team. Further, retaining the position of the leak detector after it has been installed is another challenge.

In other words, the leak detection systems known in the art are not suitably adapted to be precisely and securely positioned.

U.S. Pat. No. 7,918,126 discloses a leak detection system for precise detection of leakage of subsea materials such as hydrocarbons, hydraulic fluids, chemicals. It includes a plurality of sensors and a controller for receiving leak detection data from such sensors. It directs the sensing activities of the sensors, based on the data. However, it does not teach precisely and securely location of the system for leak detection, because it is not adapted to be so positioned and moreover it involves complex constructional network.

Similarly, U.S. Pat. No. 4,282,487 discloses a hydrocarbon detection system, but here again is not disclosed how the system is adapted to be precisely and securely positioned for precise detection of leakage. Rather, it generally states under "Background of the invention" that it is desirable that a plurality of detection units should be located at potential locations of hydrocarbon escape.

To take care of the concerns as stated in the preceding paragraphs, it has been common knowledge that leak detection systems are often located in the ceiling of subsea assemblies such as X-mas trees. The motive is to arrest all leak detections coming out from such units. However, such positioning results in faulty detection, in as much as leakage of hydrocarbons such as oil and gas above the X-mas tree are not detected.

Further, the construction of such prior art leak detection systems does not allow for suitable and secure location for precise detection. Additionally, due to their constructional disadvantage, prior art subsea leak detection systems cannot be easily installed, or for that matter retrieved after installation, for maintenance or replacement. This is for example, due to the limited space between the X-mas tree roof and X-mas tree, the desired location of installation.

Accordingly, there is a need for a subsea leak detection system, which by virtue of its simple construction is adapted to be suitably and securely located/installed for precise detection of leakage of hydrocarbons.

The present invention meets the above long felt need and other associated needs as will be clear to persons skilled in the art from the following.

OBJECTS OF THE INVENTION

The principal object of the present invention is to provide a subsea leak detection system which is adapted to be precisely and securely installed at a suitable subsea location, by virtue of its simple and unique construction, for precise detection of leakage of hydrocarbons and other materials.

It is another object of the present invention to provide a subsea leak detection system which is simple in construction comprising mutually balanced components, easy to install and very cost effective, without compromising on accuracy.

A further object of the invention is top provide a leak detection system that is less (if at all) depending on tolerances in distance between the subsea structure and the protective structure.

It is also an object for the present invention to provide a leak detection system that will not transfer impact forces to the subsea structure of the protective structure is hit by falling objects or otherwise subject to excessive forces.

Another object of the present invention is to provide a subsea leak detection system which can be easily accessed for example by an ROV, for installation and for retrieval after completion of operation or for maintenance/replacement.

It is another object of the present invention to provide a subsea leak detection system which is adapted to send a signal to the leak management team for initiating rectifying steps, in the event of detection of leakage.

It is a further object of the present invention to provide a subsea leak detection system which is adapted to ignore natural seepage from sea bed.

It is a further object of the present invention to provide a method for suitably installing a subsea leak detection system having all advantages as stated hereinbefore under the heading "Objects of the invention" for precise detection of leakage of hydrocarbon and other materials, during subsea operation.

How the foregoing objects are achieved and some other advantageous features, still not disclosed in prior art will be clear from the following non-limiting description.

All through the specification including the claims, the words, "subsea", "connector", "subsea assembly", "X-mas tree", "floating unit", "hatches", "anchor", "hydrocarbon (including oil and gas)", "subsea material", "leak detection system", "production operation", "subsea operation", "buoy" are to be interpreted in the broadest sense of the respective terms and includes all similar items in the field known by other terms, as may be clear to persons skilled in the art. Restriction/limitation, if any, referred to in the specification, is solely by way of example and understanding the present invention.

SUMMARY OF THE INVENTION

According to a first aspect of the present invention there is provided a subsea leak detection system for an off-shore operation facility, comprising at least a leak detector operatively connected to a controller located on a subsea assembly. According to the invention, the system is provided with a floating member on which the leak detector is suitably attached. The floating member is adapted to be installed and stably positioned, above the assembly In accordance with a preferred embodiment of the first aspect of the present invention the assembly is an X-mas tree having a template hatch above its roof for collection of hydrocarbon leakages and the controller is a subsea control module unit on the X-mas tree, connected by connectors such as cables, with said leak detector.

More preferably, the leak detector is a capacitive sensor type leak detector.

According to another preferred embodiment of the first aspect of the present invention the floating member is a buoy secured to a locking unit by means of wires on said X-mas tree roof, such that the leak detector is positioned above said X-mas tree roof and beneath said template hatch.

Preferably, the locking unit is securely received on a guide post receptacle, on said X-mas tree roof.

According to a second aspect of the present invention there is provided a method for installation of a subsea leak detection system for an off-shore operation facility, the system comprising at least one leak detector operatively connected to a controller located on a subsea assembly, said system being provided with a floating member on which said leak detector is suitably attached. According to the method of the present invention the floating member retaining the leak detector is installed and stably positioned by appropriate means, above the assembly.

BRIEF DESCRIPTION OF THE ACCOMPANYING FIGURES

Having described the main features of the invention above, a more detailed and non-limiting description of a preferred embodiment will be given in the following with reference to the drawings, in which FIG. 1 is a perspective view of a preferred embodiment of the leak detection system according to the present invention.

Figure 1:
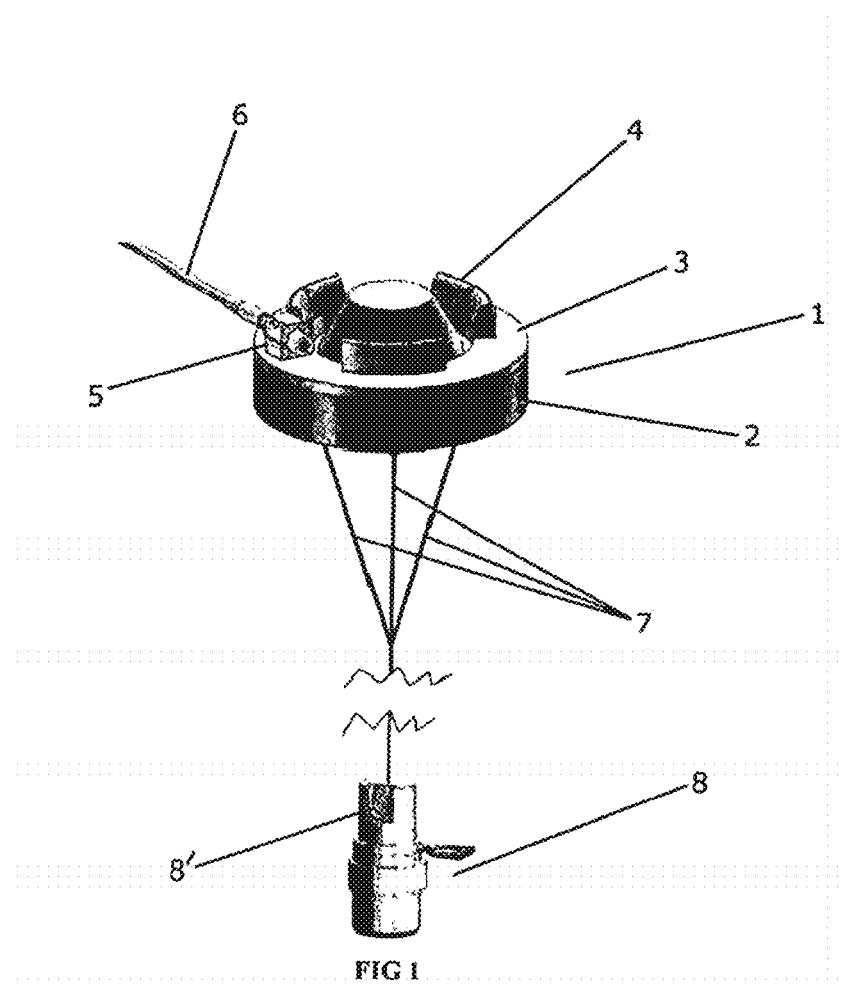
Figure 2:
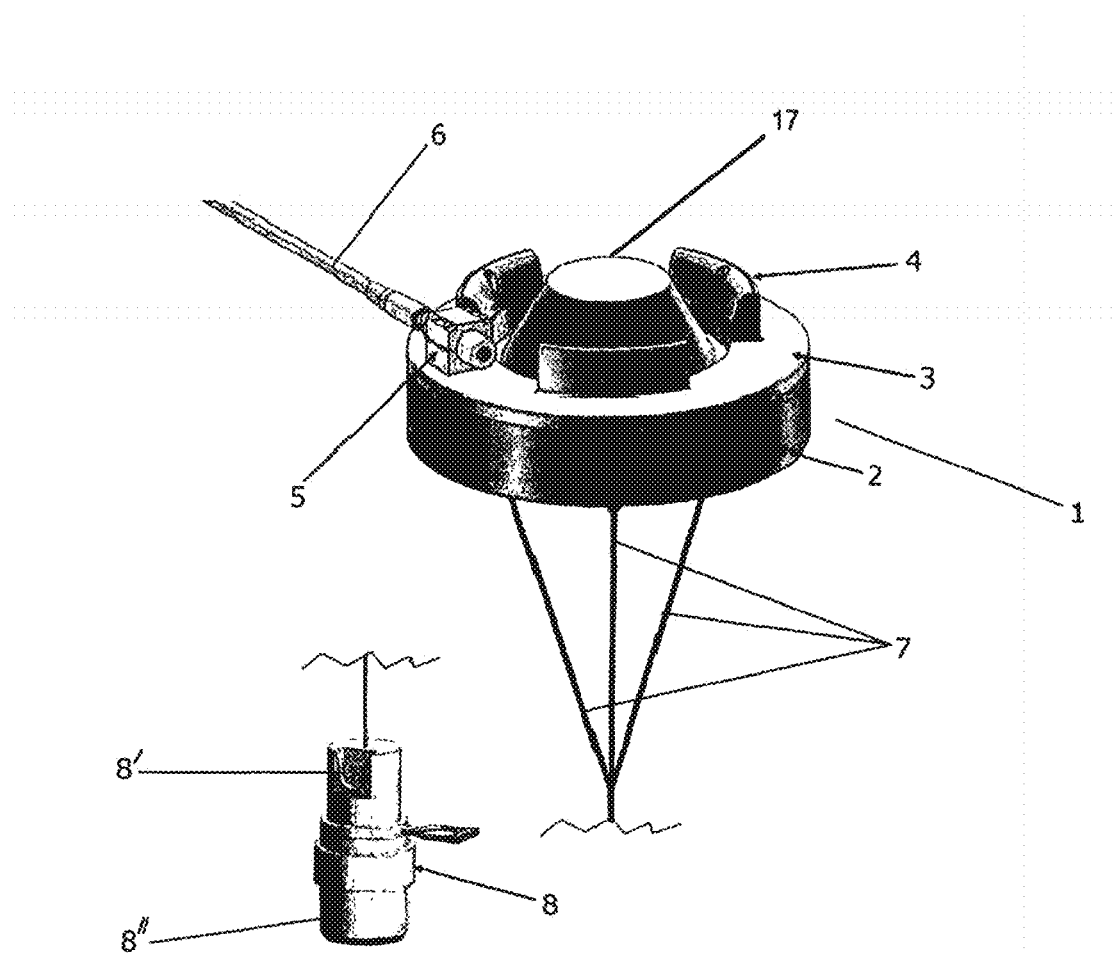
FIG. 2 illustrates an enlarged view of the leak detection system shown in FIG. 1.
Figure 3:
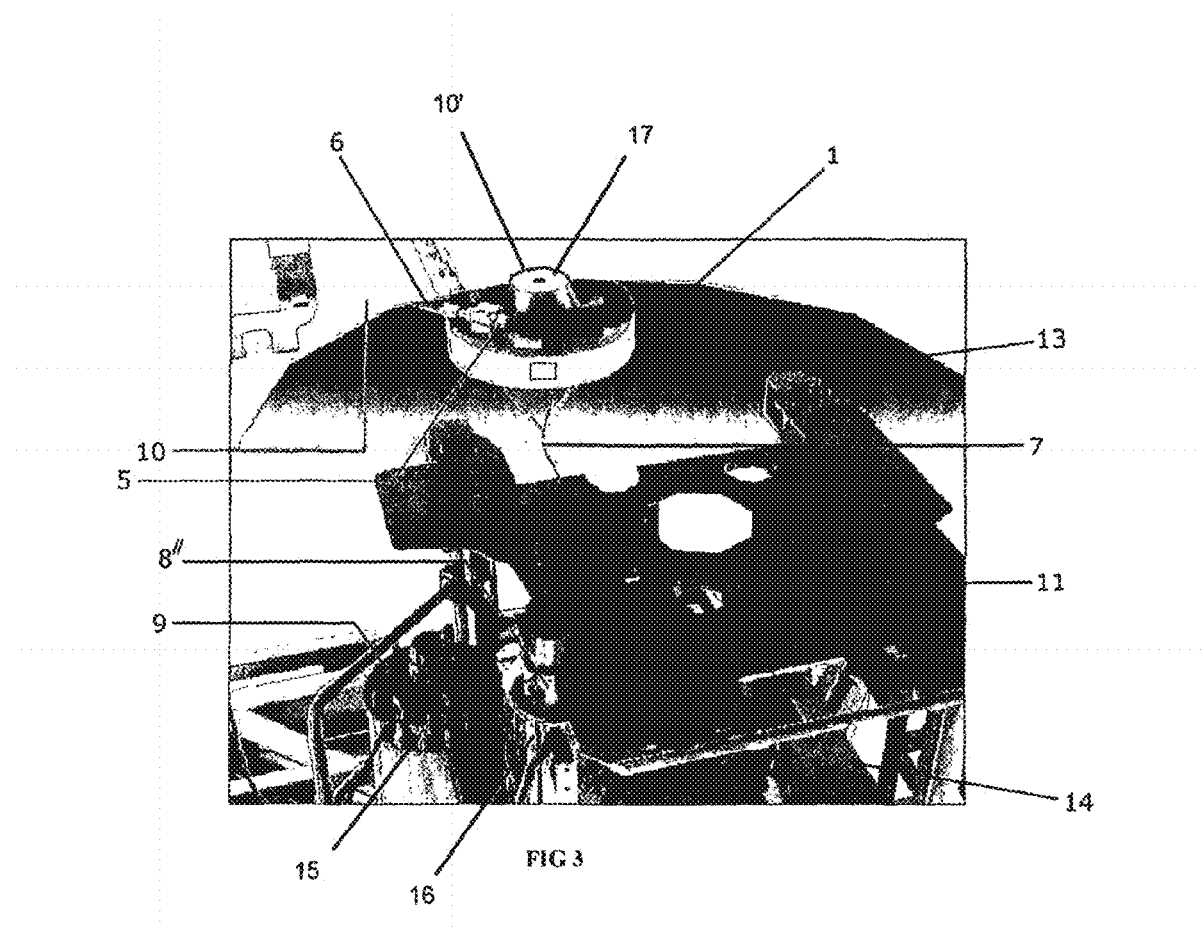
FIG. 3 illustrates the leak detection system shown in FIGS. 1 and 2 in installed position.

FIGS. 4(*a*) and 4(*b*) illustrate two consecutive stages of installation of the leak detection system shown in FIGS. 1, 2 and 3.

Figure 4A:
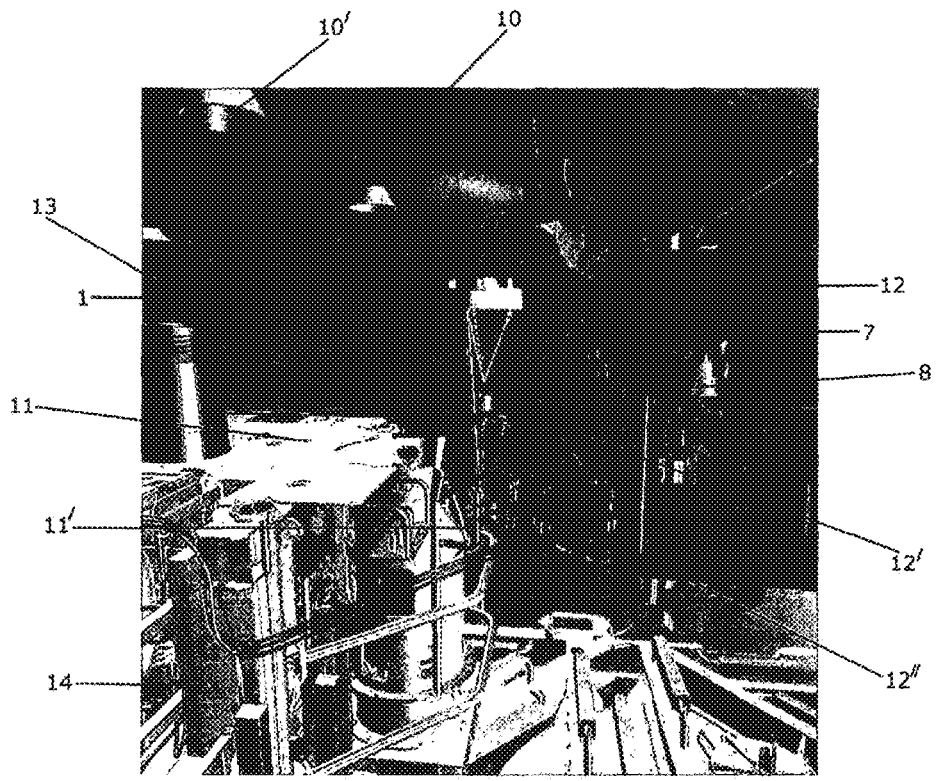
Figure 4B:
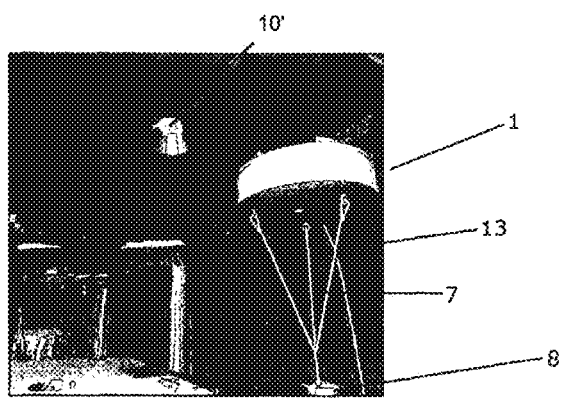
Figure 5:
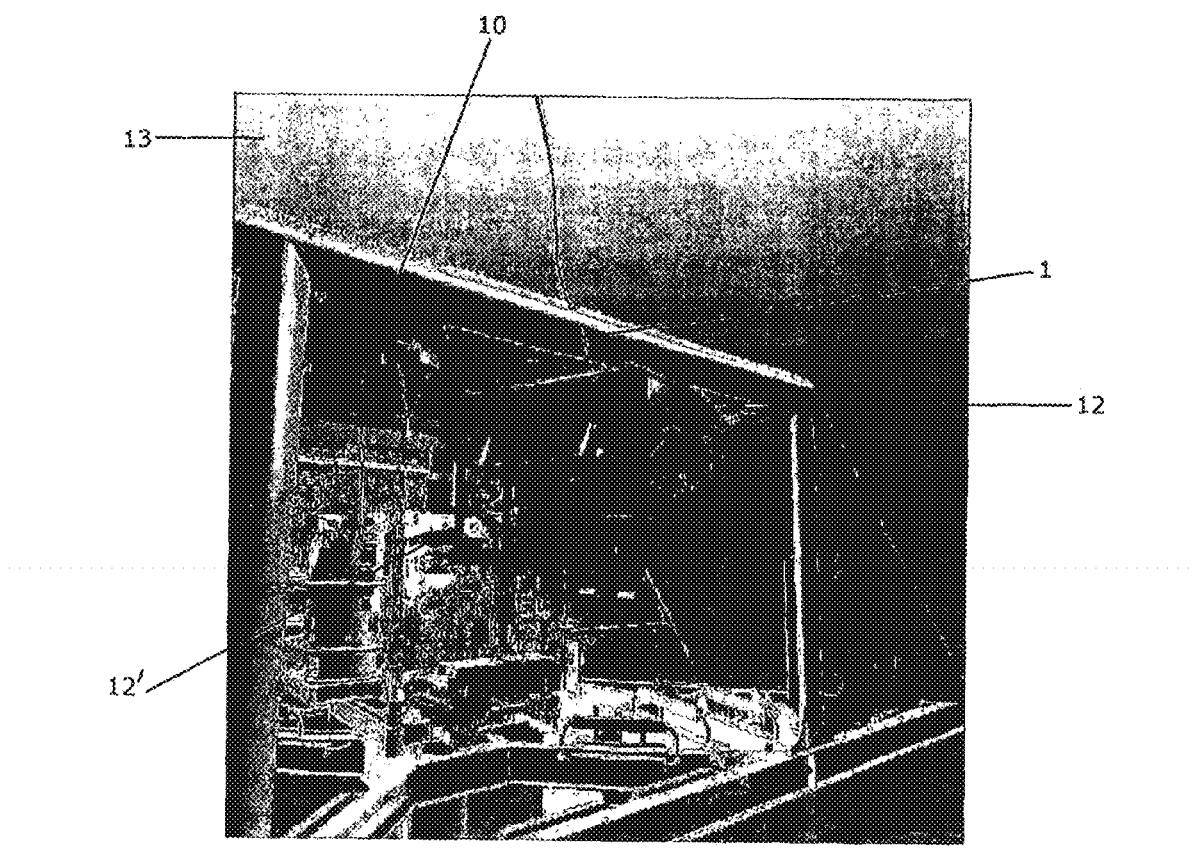

FIG. 5 illustrates a step of installation immediately consecutive to the step shown in FIG. 4(*b*), when the leak detection system of the present invention is almost installed in position.

DETAILED DESCRIPTION OF ILLUSTRATIVE EMBODIMENT

The following provides a detailed non-limiting description of a preferred embodiment of the leak detection system according to the present invention which is purely exemplary and non-limiting.

In the above context, it is hereby clarified that hereinbefore and hereinafter, the present invention as well its technical background, prior art already known, are explained with reference to hydrocarbons and X-mas trees. It should be understood that these are all limitations for the sake of explanation. The present invention pertains to all types of leakage detection under water such as hydrocarbons, hydraulic fluids/chemicals and so on, or any fluid whose Specific Gravity is lower than sea water. Further, the present invention is applicable in respect of all types of units, installations, equipments and subsea assemblies such as X-mas trees, production manifolds and so on, as known to persons skilled in the art, involved in hydrocarbon recovery by offshore operations. Reference to subsea hydrocarbon production operations, is purely exemplary and non-limiting.

As stated before, the present invention proposes a simple subsea leak detection system, which, unlike the leak detection systems hitherto known, can be precisely and securely located in subsea, for optimal detection of hydrocarbon leakage, during subsea operation.

FIG. 1 is a perspective view of the leak detection system. It comprises of a floating unit or buoy 1, which is connected to a locking unit 8, by means of wires 7. FIG. 2 is a further enlarged view of the system shown in FIG. 1, where like reference numerals represent like features. It shows the capacitive leak detector 5 with jumper, positioned on the distance ring 3 of the buoy 1. Attached to the leak detector 5 is a cable 6, which connects the leak detector 5 with a plug 15 (se FIG. 3). The buoy is also provided with impact absorbing pads 4, preferably made of rubber on its top portion. The buoy also has a buoyancy element 2 beneath the ring 3. The buoyancy element 2 provides positive upward buoyancy to the buoy.

The locking unit 8 is provided with a lower lock plug 8" and a slot 8'. The functions of these and also the other parts are explained with reference to the subsequent figures, where like reference numerals represent like constructional features.

It is common knowledge that templates involves protective structures for subsea assemblies such as X-mas trees and manifolds and template hatches are designed to protect the equipment below. Template hatches may also be used to collect small amounts of oil and gas from leakages. Further, such template hatch is particularly helpful to arrest the leakages which escape upwards undetected, so that such leakages may be redetected.

FIG. 3 illustrates a position where the leak detection system is optimally installed. This figure, illustrates how the leak detection system according to the present invention is beneficial. A close look at FIG. 3 will reveal that the buoy 1 is located beneath the X-mas tree template hatch 10 and above the X-mas tree roof 11. This position is beneficial, because the oil and gas leakage above the X-mas tree roof 11 will be detected by the leak detector 5, positioned on the floating buoy 1. Of course, the leak detector 5 identifies all leakages coming out from beneath it, barring the natural seepages from the sea bed.

The buoy 1 is guided, preferably, by an ROV, so that the leak detector 5 is placed just beneath the X-mas tree template hatch 10 but above the X-mas tree roof top 11. This is explained in detail later, with reference to FIGS. 4a, 4b and 5

The location of the leak detector 5, beneath the ceiling of the hatch 10 ensures detection of leakage from any equipment below the hatch 10. Further, the leak detector 5 is located about 5 cm below the ceiling of the hatch 10. Natural leakage from sea bed, being low in volume, if allowed to accumulate, take some time to fill this gap. So the spill from natural leakage has enough time to pass through small openings 10' (best shown in FIG. 4(a)) in the hatch 10, without being accumulated in a sufficient amount to reach the level of the capacitor of the leak detector 5.

Thus a false signal being is sent to the leakage management team due to natural leakage is largely prevented. This is also facilitated by the fact that the minor seepages from the seabed do not cause significant change in the dielectric constant of the surrounding sea water. The leak detector 5 is set at a certain threshold value adapted to ignore such insignificant changes in the dielectric constant of the surrounding media. Hence, such natural seepages escape undetected through the openings 10' (best shown in FIG. 4a).

Now the different units of the leak detection system will be explained. It is clear from FIG. 3 that the wires 7 attach the buoy 1 to the locking unit 8. The locking unit is attached in an anchored manner on the X-mas tree roof top 11. For that purpose, the lower plug unit 8" of the locking unit 8 is adapted to mate with a guide post receptacle 16 on the X-mas tree roof 11. Thus, the locking unit 8 being securely locked on the roof 11 anchors the buoy 1.

The buoy 1 has a conical top portion 17 which is adapted to mate with a funnel shape opening 10' in the hatch 10.

The template hatch 10, as explained hereinbefore facilitates collection of oil and gas leakages and is particularly helpful to arrest the leakages which escape upwards undetected, so that such leakages may be redetected.

The buoy is held in position on installation beneath the template hatch 10 by its positive upward buoyancy and by the mating of the conical portion 17 with the opening 10'. The locking unit 8 is heavier than the buoyancy of the buoy 1 and is locked to the guide post receptacle 16, thus preventing unintentional drift off of the leak detection device.

The leak detector 5 is connected by the cable 6 and the plug 15 to a sub sea control module 9 (hereinafter referred to as SCM) located on the X-mas tree. The slot 8' of the locking unit 8 acts as a secured parking space for the free end of the connector 15 when not in use, for example during removal of the whole unit.

In the preferred embodiment hereinbefore and hereinafter described, the leak detector 5 is a phase capacitive leak detector probe. But this is not consequential to the present invention and other types of sensors may be applied as well, as known to persons skilled in the art.

The leak detector 5 thus applies capacitive sensing for identifying change in the dielectric constant in the surrounding medium. So, it has to remain in physical contact with the media to detect. This is not consequential to the present invention as explained in the preceding paragraph and further elaboration is not provided, as it is known to persons skilled in the art. Due to similar reasons, the role of the SCM 9 is not elaborated. Obviously, the leak detector 5 is connected to the SCM 9, which sends signals to the surface so that the leak management team can initiate rectifying measures, in the event of detection of leakage.

It is the judicious construction of the leak detection system, involving the floating unit 1, anchored by the locking unit 8 on a X-mas tree roof top 10, such that the leak detector 5 is beneath the template hatch 10 but above the X-mas tree roof top 11, which constitutes the crux of the invention. The objective of securely placing the leak detector 5 below the template hatch 10 but above the X-mas tree roof top 11 is achieved by this unique but simple construction. The leak detector 5 is adapted to be installed approximately 5 cm below the template hatch 10.

How the installation takes place will now be elaborated with reference to FIGS. 4a, 4b and 5.

As shown in FIG. 4a the buoy 1 is guided by an arm 12' of an ROV 12 beneath the X-mas tree template hatch 10, so that the leak detector 5 is placed just beneath the X-mas tree template hatch 10, but above the X-mas tree roof top 11. One arm 12" of the ROV 12 is firmly attached to a fixed handrail 11' on the body of the X-mas tree 14. The whole unit is so constructed such that the unit in its entirety is adapted to be installed say, just 5 cm below the template hatch 10 and the unit by virtue of the buoyancy and unique balancing between components retains its position.

The installation is being shown at a stage when the hatch 10 is closed. This figure also shows the openings 10' in the hatch ceiling, through which the seepages from the sea bed escape can without being detected by the leak detector 5. As clearly shown in FIG. 4a, the floater 1 is secured by wires 7 to the locking unit 8, during ROV operations subsea (for transport and positioning).

The wire 7 prevents unintentional drift-off, should the template hatch 10 be opened without prior removal of the buoy 1 and the associated components namely, the leak detector 5, the cable 6, the wires 7 and the locking unit 8. During transport, the free end of the plug 15 is securely docked into the slot 8' (best shown in FIGS. 1 and 2) of the locking unit 8.

FIG. 4b shows the next stage where the leak detection system is brought further towards the desired location in the opening 10' below the hatch 10. FIG. 5 shows the next stage when the buoy 1 is installed at the desired location. The pads 4 rest against the hatch ceiling 10. Hence, the ROV 12 is retracted back.

The buoy does not need to be fixed to the hatch ceiling, but may be allowed to float within the boundaries of the ceiling.

If a hatch is opened without first removing the leak detector system, the buoy 1 will float up until the wires 7 are taut. The locking unit 8 will prevent the buoy from ascending further. Ideally, the leak detection system should then be removed and not installed again until the hatch 10 is closed. However, if the hatch 10 is closed again without the leak detection system first being removed, the buoy 1 will be pushed down by the hatch and lie under the hatch quite safely. It will likely not be in a correct position, but it is a simple task for an ROV to reposition the buoy 1 to one of the openings 10'. This means that the leak detection system will be kept safe irrespective of the movement of the hatch 10.

When, FIGS. 3, 4a, 4b and 5 are construed with reference to the preceding description, it would be clear to persons skilled in the art that the unique construction of the leak detection system according to the present invention makes it possible to install the leak detector beneath the hatch ceiling 10 and above the X-mas tree roof 11, which was hitherto not possible. The other advantages as stated before, are derived from this unique construction as well, particularly the retaining of position of the leak detector when installed.

The position of the leak detector 5 ensures that it detects leakage as early as possible; simultaneously ensuring that false detection of seepages from sea bed is avoided. The construction facilitates easy installation and retrieval of the entire system for replacement and maintenance. The leak detection system may be installed or removed while performing operations such as well intervention and so on.

From the foregoing description and also from the appended claims it would be clear to persons skilled in the art, that all the objectives of the present invention are achieved. The technology in accordance with the present invention can be applied both in deep sea and shallow sea and can function irrespective of the underwater condition. Further, it should be understood that only one leak detection system located above an X-mas tree is shown. Ideally, there should be a plurality of such leak detection systems installed above subsea assemblies during subsea operation, so that leak detection is done in a reliable manner and appropriate signals are sent to the leak management team, for effecting corrective measures. The present invention encompasses this aspect as well.

The present invention has been described with reference to a preferred embodiment and drawings for the sake of understanding only and it should be clear to persons skilled in the art that the present invention includes all legitimate modifications within the ambit of what has been described hereinbefore and claimed in the appended claims.

The invention claimed is:

1. A subsea leak detection system for an off-shore operation facility, the subsea leak detection system comprising:
    a leak detector operatively connected to a controller located on a subsea assembly;
    a floating member on which said leak detector is attached;
    wherein said floating member is adapted to be installed and stably positioned, above said subsea assembly;
    wherein said subsea assembly comprises a X-mas tree and a protective structure comprising a template hatch extending above the X-mas tree;
    wherein the protective structure acts to collect hydrocarbon leakages;
    wherein said floating member is a buoy secured to an anchor unit via wires; and
    said leak detector is positioned above a roof of said X-mas tree and beneath said template hatch.

2. The subsea leak detection system according to claim 1, wherein said controller is a subsea control module unit on said X-mas tree.

3. The subsea leak detection system according to claim 1, wherein said leak detector is a capacitive sensor type detector.

4. The subsea leak detection system according to claim 1, wherein said anchor unit is adapted to be securely received in a guide post receptacle on said X-mas tree roof.

5. The subsea leak detection system according to claim 1, wherein the floating member comprises a conical top portion adapted to be received in a receptacle in the template hatch.

6. A method for installation of a subsea leak detection system for an off-shore operation facility, said subsea leak detection system comprising a leak detector operatively connected to a controller located on a subsea assembly, said subsea leak detection system comprising a floating member on which said leak detector is suitably attached, the method comprising:
    installing and stably positioning the floating member retaining the leak detector in a receptacle under a template hatch, so that the floating member is held in place in the receptacle by buoyancy only;
    placing the leak detector at a specific distance under the template hatch;
    letting leakage products escape from under the template hatch at a rate superseding the leakage rate of natural seepage from the ground; and
    collecting leakage products, in excess of the leakage rate of natural seepage, under the template hatch until the level of collected leakage products reach the leak detector.

7. The method of claim 6, comprising connecting the floating member to a locking unit and connecting the locking unit to a fixed structure below the template hatch.

\* \* \* \* \*